(12) United States Patent
Pautard-Cooper et al.

(10) Patent No.: US 6,444,190 B2
(45) Date of Patent: *Sep. 3, 2002

(54) REDUCTION COMPOSITIONS AND PROCESSES FOR MAKING THE SAME

(75) Inventors: Anne Pautard-Cooper, Tarpon Springs, FL (US); Eric John Granger, Charlotte, NC (US); Philip Franklin Sims, Cherryville, NC (US); James Anthony Schwindeman, Lincolnton, NC (US); John Francis Engel, Belmont, NC (US); Terry Lee Rathman, Gastonia, NC (US)

(73) Assignee: FMC Corporation, Philadelphia, PA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/262,093

(22) Filed: Mar. 4, 1999

Related U.S. Application Data

(63) Continuation-in-part of application No. 09/051,813, filed on Apr. 15, 1998, now abandoned, and a continuation-in-part of application No. 08/817,003, filed on Mar. 31, 1997, now abandoned.
(60) Provisional application No. 60/026,552, filed on Sep. 23, 1996, and provisional application No. 60/001,857, filed on Aug. 3, 1995.

(51) Int. Cl.⁷ .................. C01B 6/24; C07D 211/22
(52) U.S. Cl. .................. 423/644; 546/220; 546/240
(58) Field of Search .................. 423/644; 546/220, 546/240

(56) References Cited

U.S. PATENT DOCUMENTS

| | | | |
|---|---|---|---|
| 2,576,311 A | 11/1951 | Schesinger et al. | |
| 2,920,935 A | 1/1960 | Finholt | |
| 3,162,508 A | 12/1964 | Bragdon et al. | |
| 3,180,700 A | 4/1965 | Robinson | |
| 3,207,570 A | 9/1965 | Nöth | |
| 3,290,123 A | 12/1966 | De Guiduci et al. | |
| 3,337,308 A | 8/1967 | Verdieck et al. | |
| 3,353,930 A | 11/1967 | Clasen et al. | |
| 3,387,933 A | 6/1968 | Snyder et al. | |
| 3,387,947 A | 6/1968 | Grendel | |
| 3,505,036 A | 4/1970 | Lindsay | |
| 3,556,740 A | 1/1971 | Murib | |
| 3,627,763 A | * 12/1971 | Jaeggi et al. | 544/153 |
| 4,512,966 A | 4/1985 | Nelson | |
| 4,902,801 A | 2/1990 | Faruk et al. | |
| 5,258,517 A | 11/1993 | Zepp et al. | |
| 5,730,952 A | * 3/1998 | Rathman | 423/644 |
| 5,936,090 A | * 8/1999 | Oautard-Cooper | 546/220 |

FOREIGN PATENT DOCUMENTS

| | | |
|---|---|---|
| CA | 595782 | 4/1960 |
| DE | 1 808 078 | 11/1968 |
| EP | 0 223 334 | 5/1987 |
| EP | 0 374 675 | 6/1990 |
| FR | 1 245 361 | 9/1960 |
| GB | 830717 | 3/1960 |
| GB | 905985 | 9/1962 |
| GB | 820513 | 9/1969 |
| JP | H3-200762 | 9/1991 |
| WO | WO 94/21609 | 9/1994 |
| WO | WO 97/05879 | 2/1997 |
| WO | WO 97/06097 | 2/1997 |

OTHER PUBLICATIONS

Robin son et al. "lithium. beryllium and magnesiu alanates" CA 67:118688, 1967.*
Ninomya et al. "Preparation of high purity organophosphine compounds" CA 121:109269, 1994.*
Cotton et al. "Advanced inorganic chemistry" Wiley & Sons, p. 222, 1995.*
L. Weber, "Functionalization of Living Polymers—Results and Problems," *Makromol. Chem. Macromol. Symp.* 3, 317–329 (1986).
J. Abraham, et al., *Eur. J. Med. Chem..*, 28(3), 231–234 (1993).
Y.S. Gyoung, et al., *J. Korean Chem. Soc.*, 35(3), 296–298 (1991).
JP07173173, Jul. 11, 1995 (abstract only).
J.E. Macor, et al., *J. Med. Chem.*, 37, 2509–2512 (1994).
McMurry, J.E. et al., "Titanium–Induced Reductive Coupling of Carbonyls of Olefins," *J. Org. Chem.*, 1978, 43 (17), pp. 3255–3266.
Greenwood, N.N. et al., Chemistry of the Elements, 1984, Pergamon Press, pp. 256–261.
Brown, H.C. et al., "Forty Years of Hydride Reductions," *Tetrahedron*, 1979, 35 , pp. 567–607.
E.C. Ashby, et al., "Direct Synthesis of Complex Metal Hydrides," *Inorganic Chemistry*, vol. 2, No. 3, Jun., 1963.

* cited by examiner

*Primary Examiner*—Ceila Chang
(74) *Attorney, Agent, or Firm*—Myers Bigel Sibley & Sajovec, P.A.

(57) ABSTRACT

Novel reduction compositions are prepared from an active hydride, an additive, and a Lewis base in a hydrocarbon solvent. Such compositions can provide a superior reducing system for organic substrates.

28 Claims, No Drawings

REDUCTION COMPOSITIONS AND PROCESSES FOR MAKING THE SAME

CROSS-REFERENCE TO RELATED APPLICATIONS

This application is a continuation-in-part application of commonly owned U.S. application Ser. No. 08/817,003, filed Mar. 31, 1997, now abandoned, the entire disclosure of which is hereby incorporated by reference, and is related to commonly owned provisional application Ser. No. 60/001,857, filed Aug. 3, 1995 and claims the benefit of the earlier filing date of this application under 35 USC §119(e), and is also a continuation-in-part application of commonly owned U.S. application Ser. No. 09/051,813, filed Apr. 15, 1998, now abandoned, the entire disclosure of which is incorporated by reference, which is related to commonly owned provisional application Ser. No. 60/026,552, filed Sep. 23, 1996, and claims the benefit of the earlier filing date of this application under 35 U.S.C. §119(e).

FIELD OF THE INVENTION

This invention relates to novel compositions for reduction of organic substrates, and processes for preparing and using the same.

BACKGROUND OF THE INVENTION

There are a wide variety of reducing agents available for organic synthesis. For example, sodium borohydride, borane, lithium aluminum hydride and hydrogen are all employed to perform reductions industrially. Lithium aluminum hydride ($LiAlH_4$) is a powerful reducing agent, soluble in organic solvents, and has found wide utility in organic synthesis. A wide variety of functional groups are reduced with this reagent, including aldehydes, ketones, esters, amides, epoxides, nitrites and imides. However, the expense of lithium aluminum hydride prevents its wider industrial employment.

A variety of synthetic methods exist for the commercial preparation of lithium aluminum hydride. One method involves the metathesis of sodium aluminum hydride ($NaAlH_4$) with lithium chloride to form lithium aluminum hydride and sodium chloride (equation 1). Another method is the hydrogenation of a mixture of lithium (or lithium hydride) and aluminum to generate lithium aluminum hydride (equations 2 and 3). There are several others variations of equations 1–3 as well as from aluminum chloride and alkali salts and hydrides (equations 4 and 5). It should be noted that preparations of lithium aluminum hydride are never targeted for the preparation of a mixed alkali aluminum hydride such as a mixture of lithium and sodium aluminum hydrides.

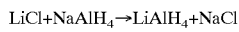    1.

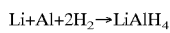    2.

    3.

    4.

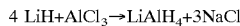    5.

All of these preparations are typically conducted in an organic solvent, such as toluene, diethyl ether, or tetrahydrofuran. Also, at the conclusion of the reaction, the reaction mixture is laboriously filtered to remove the unreacted starting materials and/or by-product inorganic salts. These filtrations are time consuming, the equipment is capital intensive, and some of the lithium aluminum hydride product adheres to the solids, which reduces the yield. The solid by-products and starting materials are very hazardous and must be handled, recycled, and quenched very carefully.

SUMMARY OF THE INVENTION

It has been discovered that a composition prepared from an active hydride, an additive, and a Lewis base, optionally in a hydrocarbon solvent, can provide a superior reducing system for organic substrates. For example, a composition prepared from 60 mole % tetrahydrofuran as the Lewis base, 10 mole % lithium chloride as the additive, 10 mole % sodium aluminum hydride as the active hydride, and 20 mole % toluene can afford excellent yields in standard organic reductions. In addition, the compositions of the invention are non-pyrophoric and are more thermally stable than pure THF solutions of sodium aluminum hydride ($NaAlH_4$) or lithium aluminum hydride ($LiAlH_4$).

The novel compositions of the invention can be prepared by initially adding the Lewis base to the additive. The hydride species can then be added, optionally in the hydrocarbon solvent. The mixture can then be optionally heated to the reflux temperature (or less), typically from about thirty minutes to about four hours.

The present invention also provides processes for the reduction of organic substrates using the compositions of the invention.

DETAILED DESCRIPTION OF THE INVENTION

Various active hydrides, including metal hydrides such as sodium aluminum hydride, trisodium aluminum hexahydride, and the like and mixtures thereof can be employed as the active hydride component. Examples of useful additives include, but are not limited to, lithium chloride, lithium bromide, aluminum trichloride, titanium tetrachloride, titanium tetrabromide, lithium alkoxides, lithium alkoxides of chiral alcohols (such as menthol), lithium dialkylamides, lithium dialkyl amides of chiral amines (such as (+) bis-[(R)-1-phenethyl]amine), and the like and mixtures thereof. Examples of useful hydrocarbon solvents include, but are not limited to, pentane, hexane, heptane, cyclohexane, decane, toluene, xylenes, ethylbenzene, cumene, cymene, and the like and mixtures thereof. Examples of useful Lewis bases include, but are not limited to, tetrahydrofuran, 2-methyltetrahydrofuran, diethyl ether, dibutyl ether, methyl t-butyl ether (MTBE), 1,2-diethoxyethane, 1,2-dimethoxyethane, triethylamine, tributylamine, N, N, N', N'-tetramethylethylenediamine (TMEDA), diisopropylethylamine, and the like and mixtures thereof.

Typical concentrations (mole %) of the components used to prepare the reducing composition of the invention are listed in the table below.

| COMPONENT | MINIMUM | MAXIMUM |
|---|---|---|
| Lewis Base | 45 | 80 |
| Solvent | 0 | 30 |
| Additive | 5 | 20 |
| Hydride | 5 | 20 |

The novel compositions of the invention can be prepared by initially adding the Lewis base to the additive. The hydride species can then be added, optionally in the hydrocarbon solvent. The mixture can then be optionally heated to the reflux temperature (or less) for a few hours, typically from about thirty minutes to about four hours.

In one advantageous embodiment of the invention, the novel composition is prepared by adding a slurry of sodium aluminum hydride/toluene to a slurry of lithium chloride/tetrahydrofuran. Because the addition is very exothermic, care should be taken. When using the specific reagents sodium aluminum hydride and lithium chloride, the reagents must be combined in a precise manner to result in reduction product yields comparable to that of lithium aluminum hydride. Otherwise, reduction product yields comparable to that of sodium aluminum hydride result.

When using sodium aluminum hydride as a starting material, the composition of the invention is also unique as it is prepared from a slurry of sodium aluminum hydride in hydrocarbon solvent (i.e., about 80 weight percent (wt %) or less sodium aluminum hydride) and a minimal amount of tetrahydrofuran, in contrast to solid or damp cake forms of sodium aluminum hydride. For example, the slurry can be a commercially available slurry of 40 wt % sodium aluminum hydride in toluene. The use of a hydrocarbon solvent alone, such as toluene, without a Lewis base, such as tetrahydrofuran, can hinder the preparation of this effective, novel composition.

Although not wishing to be bound by any explanation of the invention, it is believed that the composition of the invention can include starting materials, counterion exchange products, complexes of starting materials and/or counterion exchange products, and mixtures thereof.

The novel reduction composition of this invention can also be characterized by its particle size distribution. For example, typical particle size distribution of a novel reduction composition in accordance with the invention prepared from 56.9 mole % tetrahydrofuran as the Lewis base, 15.7 mole % lithium chloride as the additive, 12.6 mole % sodium aluminum hydride as the active hydride, and 14.8 mole % toluene was determined on a Malvern MasterSizer. The mean diameter for the reduction composition is around 350 $\mu$m and the median is 400 $\mu$m. By comparison, the particle size distribution of sodium aluminum hydride exhibits a mean diameter at 216 $\mu$m and a median at 200 $\mu$m. The particle size distribution of lithium chloride exhibits a mean diameter at 424 $\mu$m and a median at 448 $\mu$m.

It has also been found that this same representative reduction composition slurry sample can be analyzed for sodium, lithium and aluminum by ICP (Inductively Coupled Plasma) and for chloride by wet titration. This data confirms the appropriate proportions of NaAlH$_4$ and LiCl combined during the preparation of this novel reduction composition. This is especially important when the sodium aluminum hydride charge cannot be accurately determined, for example, on large scale. Example ICP and chloride analyses are represented below. Chloride analysis is faster and combined with a hydride content analysis, should confirm the ratio of NaAlH$_4$ and LiCl.

| Theoretical | Lot# 10976 | Lot# 11011 |
|---|---|---|
| 11.4% NaAlH$_4$ | 10.9% by Na | 11.0% by Na |
|  | 11.5% by Al | 11.7% by Al |
| 9.8% LiCl | 9.9% by Li | 9.9% by Li |
|  | 9.3% by Cl | 9.2% by Cl |

The thermal behavior of the novel reduction composition was studied in an RSST (Reactive System Screening Tool) and found to be more thermally stable than 10 wt % LiAlH$_4$/THF or 40 wt % NaAlH$_4$. The LiAlH$_4$/THF solution was found to produce a runaway reaction represented by a rapid rate acceleration when heated above 130° C. Likewise, a NaAlH$_4$/THF solution was found to produce a runaway reaction represented by a rapid rate acceleration when heated above 220° C. Whereas a similar experiment with a novel reduction composition mixture prepared from 9.7 mole % NaAlH$_4$, 16 mole % LiCl, 10.4 mole % toluene and 63.9 mole % THF showed a rate acceleration/runaway behavior only when heated above 300° C. These experiments demonstrate that the novel reduction composition formulation is safer and thus more stable than a 10 wt % LiAlH$_4$/THF solution as well as a 40 wt % NaAlH$_4$/THF solution.

In use, the organic compound to be reduced is added to the reduction composition of the invention under an inert atmosphere. Alternatively, the reduction composition can be added to the organic substrate, or the reduction composition and organic substrate added simultaneously. The reduction reaction proceeds under appropriate conditions at a temperature sufficient and for a time sufficient for the reduction reaction to proceed, generally at a temperature of about ambient to about the reflux temperature of the mixture for about one hour to about 24 hours. The reaction can be terminated by quenching the mixture, for example, by addition of water and aqueous NaOH and cooling. Work-up of the reduction reaction mixture and isolation of the reduced product can be accomplished using conventional procedures known in the art.

The compositions of the invention can be used for the reduction of a variety of organic compounds including without limitation aldehydes, ketones, esters, amides, epoxides, nitrites, and other imides. Exemplary compounds which can be reduced in accordance with the invention include (+/−) trans 3-ethoxycarbonyl-4-(4'-fluorophenyl)-N-methyl-piperidine-2,6-dione (to (+1-) trans 4-(4'-fluorophenyl)-3-hydroxymethyl-N-methylpiperidine), N-methylsuccinimide, ethyl 1-methylnipecotate, and the like.

For example, typical reducing agents and yields are listed in the table below for the reduction of (+/−) trans 3-ethoxycarbonyl-4-(4'-fluorophenyl)-N-methyl-piperidine-2,6-dione to (+/−) trans 4-(4'-fluorophenyl)-3-hydroxymethyl-N-methylpiperidine.

| REAGENT | YIELD |
|---|---|
| Sodium Aluminum Hydride | 45%[1] |
| Lithium Aluminum Hydride | 65–75%[2] |
| Composition of the Invention | 85%[3] |

Notes:
[1]See Example 4 of the present application.
[2]See Example 7 of U.S. Pat. No. 4,902,801, Process for Preparing Aryl-Piperidine Carbinols and Novel Intermediates Used in the Process, E. A. Faruk, R. T. Martin, Beecham Group, February 20, 1990.
[3]See Example 5 of the present application.

It is reported in the literature that commercial sodium aluminum hydride (NaAlH$_4$) is capable of reducing selected organic functional groups including aldehydes, ketones, esters, carboxylic acids, epoxides, amides, imides, and sulfoxides. Many times, however, the yields are lower using sodium aluminum hydride instead of lithium aluminum hydride, as demonstrated by the above table. See also Example 4 below, which demonstrates that use of sodium aluminum hydride alone as the reducing agent resulted in reduction product yields from 45 to 55%, using toluene/THF solvent mixtures and THF alone. Use of LiCl in limiting amounts (0.1 equivalent) also gave low yields (50%).

The inventors have found that the reactivity of sodium aluminum hydride can be improved by the addition of various additives. Thus, in accordance with this invention, reductions can be accomplished with sodium aluminum hydride when its activity is modified with various additives as described above. For example, the additive lithium chloride could be mixed with sodium aluminum hydride in order to produce a resulting hydride composition that performs as well as lithium aluminum hydride alone.

It is also known that LiCl can be reacted with $NaAlH_4$ in stoichiometric amounts to form lithium aluminum hydride, which is then separated from the by-product, NaCl, prior to use. This metathesis reaction, however, requires the addition of a catalyst, such as a small amount of $LiAlH_4$, to initiate the reaction, or alternatively a $NaAlH_4$ solution forming prestep. In this invention LiCl can be added in less than stoichiometric amounts, and without requiring $LiAlH_4$ as a catalyst, or a $NaAlH_4$ solution forming prestep. As discussed above, when the starting compounds include sodium aluminum hydride and lithium chloride, the order of addition of the additive is important. However, it is not currently believed that the order of addition of the additives is critical when using other starting materials, in which case it is currently believed that the additives can be added at various times during the entire reduction.

Although reductions performed with $LiAlH_4$ provide better yields than when using $NaAlH_4$ (i.e., $NaAlH_4$ without additives may be less reactive in some cases), $LiAlH_4$ is much more expensive than $NaAlH_4$. Reductions of functional groups, especially imides, employing $NaAlH_4$ in accordance with the invention, however, with the appropriate additives gave identical results as obtained when using the more costly commercial $LiAlH_4$.

The present invention also describes less expensive alternatives for organic functional group reductions, using in situ generated alkali hydride reducing agents. This aspect of the present invention overcomes prior difficulties associated with the commercial preparation of lithium aluminum hydride. It has been discovered that unfiltered solutions of lithium aluminum hydride (equations 1 to 5) are capable of reduction of functional groups, especially imides. Unfiltered lithium aluminum hydride prepared from sodium aluminum hydride and lithium chloride, or unfiltered lithium or sodium aluminum hydride prepared from the elements can be used directly in subsequent reduction of the substrate. If required for yield improvement, other additives can be added to the sodium aluminum hydride. The resulting unfiltered, in situ-prepared hydride reducing agents are used directly for reduction of a substrate in an organic solvent. Overall this process saves in number of filtration steps, causes filtrations to be safer, and reduces the handling large amounts of ethereal solvents required for the preparation of the reducing agent. The yields with the in situ reduction protocol are essentially identical to the yields obtained when the reduction is performed with filtered lithium aluminum hydride solution. Further, all functional groups that are typically reduced with filtered lithium aluminum hydride are reduced with the unfiltered lithium aluminum hydride solutions. Work-up of the reduction reaction and isolation of the reduced product involves employment of the standard procedure used for commercial lithium aluminum hydride. The inorganic by-products are most often removed by filtration or become part of any aqueous phase that may be present.

For example, reduction of (+/−) trans 3-ethoxycarbonyl-4-(4'-fluorophenyl)-N-methyl-piperidine-2,6-dione or (+/−) trans 3-methoxycarbonyl-4-(4'-fluorophenyl)-N-methyl-piperidine-2,6-dione with unfiltered lithium aluminum hydride afforded (+/−) trans-4-(4'-fluorophenyl)-3-hydroxymethyl-N-methylpiperidine in essentially the same yields and with similar impurity profiles as with commercial $LiAlH_4$.

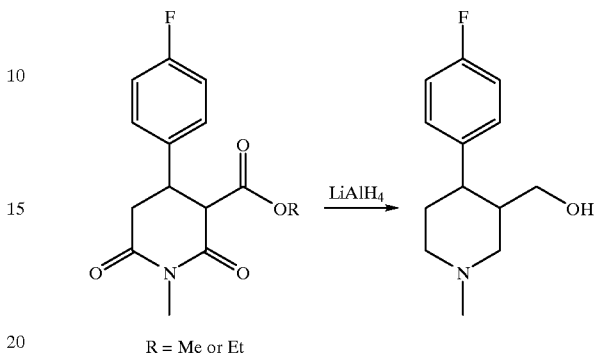

R = Me or Et

In another aspect of this invention, reductions can be accomplished with sodium aluminum hydride when its activity is modified with various additives. It is reported in the literature that commercial sodium aluminum hydride ($NaAlH_4$) is capable of reducing selected organic functional groups including aldehydes, ketones, esters, carboxylic acids, epoxides, amides, imides, and sulfoxides. Many times the yields are lower using sodium aluminum hydride instead of lithium aluminum hydride. It was found that the reactivity of sodium aluminum hydride can be improved by the addition of various additives. For example the additive, lithium chloride, could be mixed with sodium aluminum hydride in order to produce a resulting hydride that performed as well as sodium aluminum hydride with the additive, lithium aluminum hydride, or lithium aluminum hydride alone. It is known that LiCl can be reacted with $NaAlH_4$ in stoichiometric amounts to form lithium aluminum hydride (equation 1), which is then separated from the by-product, NaCl, prior to use. In this invention it was found that it is unnecessary to filter the NaCl prior to use of the in situ formed lithium aluminum hydride. Also, in this invention LiCl can be added in less than stoichiometric amounts and the NaCl is not separated from the resulting hydride. This invention shows that this filtration is unnecessary. The additives can be added at various times during the entire reduction. Although $NaAlH_4$ without additives may be less reactive in some cases, it is superior due to the high cost of $LiAlH_4$. Reductions of functional groups, especially imides, employing $NaAlH_4$ with the appropriate additives gave identical results as obtained when using the more costly, commercial $LiAlH_4$.

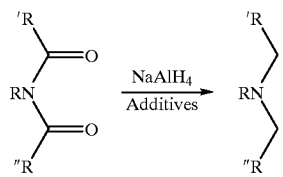

For example, reduction of (+/−) trans 3-ethoxycarbonyl-4-(4'-fluorophenyl)-N-methyl-piperidine-2,6-dione with in situ modified NaAlH4 afforded (+/−) trans-4-(4'-fluorophenyl)-3-hydroxymethyl-N-methylpiperidine in essentially the same yield and with similar impurity profile as with commercial $LiAlH_4$.

Optionally, inorganic or organic additives can be added to either reduction protocol to aid the reduction. These additives can be employed in 0.01 equivalents up to and including 5 equivalents. Examples of useful additives, which can be used in combination as well, include, but are not limited to LiCl, HCl, LiBr, AlCl$_3$, TiCl$_4$, AlBr$_3$, TiBr$_4$, LiAlH$_4$, NaBH$_4$, LiBH$_4$, LiBH(R)$_3$, NaBH$_3$ (anilide), THF-BH$_3$, LiAlH(OMe)$_3$, LiAlH(O-t-Bu)$_3$, NaAlH$_2$ (OC$_2$H4OCH$_3$), AlH$_3$; ethers such as methyl t-butyl ether, dimethoxyethane, glymes; alcohols such as methanol, ethanol, isopropanol, t-butanol, ethereal alcohols and/or their corresponding metal alkoxides; primary and/or secondary amines both aromatic and/or aliphatic and their corresponding metal amides; and tertiary amines such as tetramethylethylene diamine, triethylamine.

The following examples further illustrate the invention.

EXAMPLE 1

Preparation of Novel Reduction

Composition at Room Temperature

A 500 ml., three-necked round-bottom flask was fitted with a mechanical stirrer, a Teflon® stopper, and a Claisen adapter fitted with a dry ice condenser, a Teflon® clad thermocouple, and an argon inlet. This apparatus was dried in an oven overnight at 125° C., assembled hot, and allowed to cool to room temperature in a stream of argon. The flask was charged with 10.00 grams (0.237 mole) of anhydrous lithium chloride, and 70 ml. of tetrahydrofuran. The resultant slurry was stirred at 350 RPMs. A slight exotherm, 3° C., was observed. This slurry was stirred at room temperature for 30 minutes. A slurry of 12.80 grams (90% assay NaAlH$_4$, 0.213 mole) in 24 ml. of toluene was added. An exotherm of 9° C. was observed within four minutes.

This slurry was prepared from 15.3 mole % lithium chloride, 56.1 mole % tetrahydrofuran, 13.9 mole % sodium aluminum hydride, and 14.7 mole % toluene.

The dark gray slurry was employed in a reduction after stirring at room temperature for one hour.

EXAMPLE 2

Preparation of Novel Reduction

Composition at Low Temperature

A 500 ml., three-necked, jacketed, round-bottom flask was fitted with a mechanical stirrer, a Teflon® stopper, and a Claisen adapter fitted with a dry ice condenser, a Teflon® clad thermocouple, and an argon inlet. This apparatus was dried in an oven overnight at 125° C., assembled hot, and allowed to cool to room temperature in a stream of argon. The flask was charged with 13.80 grams (0.327 mole) of anhydrous lithium chloride, and 97 ml. of tetrahydrofuran. The resultant slurry was stirred at 350 RPMs. A slight exotherm, 3° C., was observed. This slurry was stirred at room temperature for five hours. The slurry was cooled to 0° C. with a chiller. A slurry of 13.00 grams (95% assay NaAlH$_4$, 0.229 mole) in 38 ml. of toluene was added. An exotherm of 9° C. was observed immediately.

This slurry was stirred at less than 10° C. for one hour, then allowed to gradually warm to ambient temperature overnight.

This slurry was prepared from 15.5 mole % lithium chloride, 56.8 mole % tetrahydrofuran, 10.9 mole % sodium aluminum hydride, and 16.9 mole % toluene.

The dark gray slurry was employed in a reduction after stirring at room temperature overnight.

EXAMPLE 3

Preparation of Novel Reduction

Composition at High Temperature

A 500 ml., three-necked round-bottom flask was fitted with a mechanical stirrer, a Teflon® stopper, and a Claisen adapter fitted with a dry ice condenser, a Teflon® clad thermocouple, and an argon inlet. This apparatus was dried in an oven overnight at 125° C., assembled hot, and allowed to cool to room temperature in a stream of argon. The flask was charged with 10.00 grams (0.237 mole) of anhydrous lithium chloride, and 70 ml. of tetrahydrofuran. The resultant slurry was stirred at 350 RPMs. A slight exotherm, 3° C., was observed. This slurry was stirred at room temperature for 30 minutes. A slurry of 12.80 grams (90% assay NaAlH$_4$, 0.213 mole) in 24 ml. of toluene was added. An exotherm of 9° C. was observed within four minutes.

This slurry was prepared from 15.3 mole % lithium chloride, 56.1 mole % tetrahydrofuran, 13.9 mole % sodium aluminum hydride, and 14.7 mole % toluene.

The dark gray slurry was employed in a reduction after stirring at 70° C. for two hours.

EXAMPLE 4

Comparative Example

Reduction with Sodium Aluminum Hydride

A 500 ml., three-necked, jacketed flask was equipped with a mechanical stirrer, a 125 ml. pressure-equalizing addition funnel, and a Claisen adapter fitted with a Teflon® clad thermocouple, a dry ice condenser, and an argon inlet. This apparatus was dried in an oven overnight at 125° C., assembled hot, and allowed to cool to room temperature in a stream of argon. The flask was charged with tetrahydrofuran, 70 ml. This solution was stirred at 350 RPMs and cooled to 0° C. with a circulating chiller. Sodium aluminum hydride, 12.11 grams of 95% assay (2.70 equivalents, 213 mmole) was added to the reactor. An immediate exotherm of 8° C. was noted, which quickly subsided. Toluene, 24 ml., was then added. This suspension was stirred at 0° C. for an additional thirty minutes. A dry, 250 ml., single-necked flask was fitted with a large, egg-shaped magnetic stir bar, and an argon inlet. This flask was purged with argon, then charged with 24.4 grams of 94.5% assay (+/−) trans 3-ethoxy or 3-methoxy carbonyl-4-(4'-fluorophenyl)-N-methyl-piperidine-2,6-dione (1.00 equivalent, 79 mmole) and 65 ml. of toluene. This suspension was stirred at room temperature. After all the imide-ester dissolved, the solution was transferred to the addition funnel. The 250 ml. flask was rinsed with additional toluene, 8 ml, and this was added to the addition funnel. The imide-ester solution was added dropwise. This resulted in a very exothermic reaction. The feed rate was adjusted to maintain the reaction temperature at 10–15° C. Total imide-ester feed time was 62 minutes. After the end of the feed, the reaction mixture was heated to 65° C. for two hours, then recooled to 0° C. Additional toluene, 85 ml., was added. This was followed by slow addition of 9 ml. of water. The reaction mixture got very thick at the end of this addition. Aqueous sodium hydroxide, 15%, 9 ml., was then added dropwise. The solid started to break up at the end of this addition. Water, 9 ml., was then added dropwise. At the end of this feed, the reaction mixture was warmed to 65° C. The reaction mixture was stirred at 65° C. for thirty minutes, recooled to 27° C., then the solids were collected on a Büchner funnel. The solids were reslurried with toluene (2×30 ml.). The filtrate was two layers. It was concentrated on the rotary evaporator to 250 ml., and transferred to a separatory funnel. The mixture was diluted with water (100 ml.) and toluene (100 ml.). The aqueous layer was drawn off and discarded. The organic layer was washed with water (1×100 ml.), and dried with magnesium sulfate. The desired product was isolated by precipitation from the organic layer, washed, air dried, then dried in a vacuum desiccator overnight.

This afforded a white solid, yield=8.01 grams, 45.4%.

EXAMPLE 5

Reduction with Novel Reduction Composition

A 500 ml., four-necked, round bottom flask was equipped with a mechanical stirrer, a 125 ml. pressure-equalizing addition funnel, a Teflon® stopper and a Claisen adapter fitted with a Teflon® clad thermocouple, a dry ice condenser, and an argon inlet. This apparatus was dried in an oven overnight at 125° C., assembled hot, and allowed to cool to room temperature in a stream of argon. Lithium chloride, 9.85 grams (2.64 equivalents, 232.36 mmole) was added. The flask was then charged with tetrahydroflran, 67 ml. This solution was stirred at 350 RPMs. Sodium aluminum hydride, 12.01 grams of 95% assay (2.40 equivalents, 211.24 mmole) slurried in toluene, 21 ml., was added to the reactor. The slurry composition was prepared from 15.8 mole % lithium chloride, 56.3 mole % tetrahydrofuran, 14.4 mole % sodium aluminum hydride, and 13.4 mole % toluene. Additional tetrahydrofuran, 39 ml., was added and this suspension was stirred at room temperature for fifty minutes. Toluene, 31 ml., was then added. This suspension was cooled to 10° C. and stirred for an additional five minutes. A dry, 250 ml., single-necked flask was fitted with a large, egg-shaped magnetic stir bar, and an argon inlet. This flask was purged with argon, then charged with 27.1 grams of 94.5% assay (+/−) trans 3-ethoxy or 3-methoxy carbonyl-4-(4'-fluorophenyl)-N-methyl-piperidine-2,6-dione (1.00 equivalent, 88 mmole) and 69 ml. of toluene. This suspension was stirred at room temperature. After all of the imide ester had dissolved, the solution was transferred to the addition funnel. The imide-ester solution was added dropwise. This resulted in a very exothermic reaction. The feed rate was adjusted to maintain the reaction temperature at 10–15° C. After the end of the feed, the 250 ml. flask was rinsed with additional toluene, 7 ml, and this was added to the addition funnel. The reaction mixture was heated to 75° C. for three hours, then recooled to 10° C. Additional toluene, 50 ml., was added. The speed of the agitator was increased to 500 RPMs. This was followed by slow addition of 9 ml. of water. The reaction mixture got very thick at the end of this addition. Aqueous sodium hydroxide, 15%, 9 ml., was then added dropwise. The solid started to break up at the end of this addition. Water, 18 ml., was then added dropwise. At the end of this feed, the reaction mixture was warmed to 65° C. for twenty minutes and the stirrer was slowed to 350 RPMs. The reaction mixture was then cooled to 400° C., then the solids were collected on a Buchner funnel. The solids were reslurried with toluene (2×31 ml.). The desired product was isolated by precipitation from the combined filtrates, washed, air dried, then dried in a vacuum desiccator overnight.

This afforded a white solid, yield=16.85 grams, 85.9%.

EXAMPLE 6

Reduction of N-Methyl Succinimide with NaAlH$_4$/LiCl

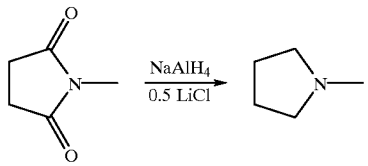

To a cooled solution of lithium chloride (0.11 mol) in THF is added NaAlH$_4$ (0.22 mol) in toluene/THF under argon. N-methylsuccinimide (0.083 mol) in THF is added holding the temperature below 15° C. After addition is complete, the reaction is allowed to warm to room temperature. After 30 minutes at room temperature reaction is heated to >40° C. for 2 hr. The reaction is then cooled to <5° C. and toluene (50 ml) is added. Water (9 ml) is then added slowly holding the temperature below 15° C. Additional H$_2$O or aqueous NaOH is used as necessary. The insoluble inorganic salts are removed by filtration. These solids are washed with additional THF or toluene to obtain a solution which contained N-methyl pyrrole, as determined by GLC analysis. Similar results were obtain using 0.02 mole of lithium chloride, but a longer heating period is required.

EXAMPLE 7

Reduction of N-methyl succinimide with

NaAlH$_4$/Lithium t-butoxide

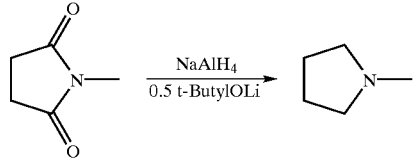

To a cooled solution of NaAlH$_4$ (0.22 mol) in toluene/THF under argon is added lithium tert-butoxide (0.11 mol) in THF. N-methylsuccinimide (0.083 mol) is added in THF (65 ml) holding the temperature below 15° C. After addition is complete, the reaction is allowed to warm to room temperature. After 30 minutes at room temperature, the reaction is heated to >40° C. for 2 hr. The reaction is then cooled to <5° C. and toluene (5 ml) is added. Water (9 ml) is then added slowly holding the temperature below 15° C. Additional H$_2$O or aqueous NaOH is used as necessary. The solid inorganic salts are removed by filtration. These solids are washed with additional THF or toluene to obtain solution which contained N-methyl pyrrole, as determined by GLC analysis.

EXAMPLE 8

Reduction of N-Methylsuccinimide

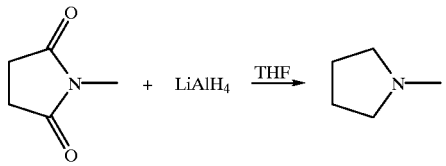

To a cooled solution of filtered or unfiltered LiAlH₄ (2 mole) under argon was added N-methylsuccinimide (1 mole) in THF. After addition was complete, reaction was heated to 40 to 50° C. for 2 hr and then stirred overnight at room temperature. The reaction was quenched by adding H₂O, and aqueous NaOH using appropriate cooling. The solution was filtered and solids were washed with fresh THF. The yields were determined by GC analysis of crude filtered reaction solutions using nonane as an internal standard. Essentially no difference in yields was observed with filtered or unfiltered LiAlH₄ solutions.

EXAMPLE 9

Reduction of Ethyl 1-methylnipecotate

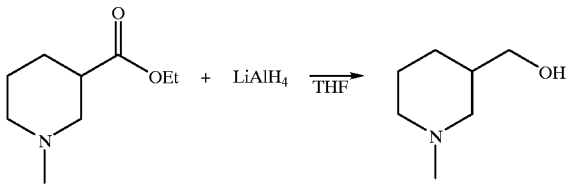

To a cooled solution of filtered or unfiltered LiAlH₄ (2 mole) under argon was added ethyl 1-methylnipecotate (1 mole) in THF. After addition was complete, reaction was heated to 40 to 50° C. for 2 hr and then stirred overnight at room temperature. The reaction was quenched by adding H₂O, and aqueous NaOH using cooling as required. The solution was then filtered and solids were washed with fresh THF. Yields were determined by GC analysis of crude filtered reaction solutions using nonane as an internal standard. Essentially no difference in yields was observed with filtered or unfiltered LiAlH₄ solutions.

EXAMPLE 10

Reduction of (+/−) Trans 3-ethoxycarbonyl-4-(4'-fluorophenyl)-N-methyl-piperidine-2,6-dione

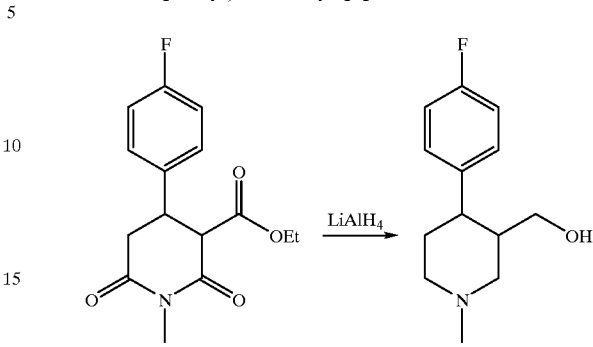

To a cooled solution of filtered or unfiltered LiAlH₄ (2.7 mol) in THF under argon as added (+/−) trans 3-ethoxycarbonyl-4-(4'-fluorophenyl)-N-methyl-piperidine-2,6-dione (1 mol) in THF. After addition was complete, reaction was heated to 40 to 50° C. for 2 hr and then stirred overnight at room temperature. The reaction was quenched by adding H₂O, and aqueous NaOH using cooling as required. The solution was then filtered and solids were washed with fresh THF. The filtrate was analyzed by NMR and HPLC. The presence of unreduced product was not detectable by ¹H NMR for either filtered or unfiltered LiAlH₄.

EXAMPLE 11

Reduction of (±) Trans-3-Ethoxycarbonyl-4-(4'-Fluorophenyl)-N-Methylpiperidin-2,6-Dione with NaAlH₄

To a cooled solution of NaAlH₄ (0.22 mol) in toluene/THF under argon was added (+/−) trans-3-ethoxycarbonyl-4-(4'-fluorophenyl)-N-methyl-piperidine-2,6-dione (0.083 mol) in THF holding the temperature below 15° C. After addition was complete, reaction was allowed to warm to room temperature. After 30 minutes at room temperature, the reaction was heated to >40° C. for 2 hr. The reaction was then cooled to <5° C. and toluene (50 ml) was added. Water (9 ml) was then added slowly holding the temperature below 15° C. Additional H₂O or aqueous NaOH were used as necessary. The solid inorganic salts were removed by filtration. These solids were washed with additional THF or toluene. The filtered solution was then concentrated to give (+/−) trans-4-(4'-fluorophenyl)-3-hydroxymethyl-N-methylpiperidine in lower yield (but similar impurity profile as with LiAlH₄) as shown by HPLC analysis. The product can be recovered by standard procedures such as trituration with a less polar solvents.

EXAMPLE 12

Comparative Example: Reduction of (A-Trans-3-Ethoxycarbonyl-4-(4'-Fluorophenyl)-N-Methylpiperidin-2,6-Dione with LiAlH₄

To a cooled solution of LiAlH₄ (0.22 mol) in toluene/THF under argon was added (+/−) trans-3-ethoxycarbonyl-4-(4'-fluorophenyl)-N-methyl-piperidine-2,6-dione (0.083 mol) in THF holding the temperature below 15° C. After addition was complete, the reaction was allowed to warm to room temperature. After 30 minutes at room temperature reaction was heated to >40° C. for 2 hr. Reaction was then cooled to <5° C. and toluene (50 ml) was added. Water (9 ml) was then added slowly holding the temperature below 15° C. Additional H$_2$O or aqueous NaOH was used as necessary. The solid inorganic salts were removed by filtration. These solids were washed with additional THF or toluene. The filtered solution was then concentrated to give (+/−) trans-4-(4'-fluorophenyl)-3-hydroxymethyl-N-methylpiperidine in higher yield (but similar impurity profile) as with NaAlH$_4$ as shown by HPLC analysis. The product can be recovered by standard procedures such as trituration with a less polar solvent.

EXAMPLE 13

Reduction of (±)-Trans-3-Ethoxycarbonyl-4-(4'-Fluorophenyl)-N-Methylpiperidin-2,6-Dione with NaAlH$_4$/LiAlH$_4$ To a cooled 50:50 mole mixture of NaAlH$_4$/LiAlH$_4$ (0.22 mol) in toluene/THF under argon is added (+/−) trans-3-ethoxycarbonyl-4-(4'-fluorophenyl)-N-methyl-piperidine-2,6-dione (0.083 mol) in THF holding the temperature below 15° C. After addition is complete, the reaction is allowed to warm to room temperature. After 30 minutes at room temperature reaction is heated to >40° C. for 2 hr. Reaction is then cooled to <5° C. and toluene (50 ml) is added. Water (9 ml) is then added slowly holding the temperature below 15° C. Additional H$_2$O or aqueous NaOH is used as necessary. The solid inorganic salts are removed by filtration. These solids are washed with additional THF or toluene. The filtered solution is then concentrated to give (+/−) trans-4-(4'-fluorophenyl)-3-hydroxymethyl-N-methylpiperidine in essentially the same yield and similar impurity profile as with LiAlH$_4$ as shown by HPLC analysis. The product can be recovered by standard procedures such as trituration with a less polar solvents.

EXAMPLE 14

Reduction of (±)-Trans-3-Ethoxycarbonyl-4-(4'-Fluorophenyl)-N-Methylpiperidin-2,6-Dione with NaAlH$_4$/LiCl.

To a cooled mixture of NaAlH$_4$ (0.22 mol) in toluene is added LiCl (0.11 mol) in THF. Note: LiCl can be added to the reactor prior to the addition of NaAlH$_4$ or after the addition of the substrate, (+/−)trans 3-ethoxycarbonyl-4-(4'-fluorophenyl)-N-methyl-piperidine-2,6-dione. Next, (+/−) trans 3-ethoxycarbonyl-4-(4'-fluorophenyl)-N-methyl-piperidine-2,6-dione (0.083 mol) is added in THF (65 ml) holding the temperature below 15° C. After addition is completed, reaction is allowed to warm to room temperature. After 30 minutes at room temperature, the reaction is heated to >40° C. for 2 hr. The reaction is then cooled to <5° C. and toluene (50 ml) is added. Water (9 ml) is then added slowly holding the temperature below 15° C. Additional H$_2$O or aqueous NaOH is used as necessary. The solid inorganic salts are removed by filtration. These solids are washed with additional THF or toluene. The filtered solution is then concentrated to give (+/−) trans-4-(4'-fluorophenyl)-3-hydroxymethyl-N-methylpiperidine in essentially the same yield and similar impurity profile as with LiAlH$_4$ as shown by HPLC analysis. The product can be recovered by standard procedures such as trituration with a less polar solvents.

EXAMPLE 15

Reduction of N-Methyl Succinimide with NaAlH$_4$/LiCl.

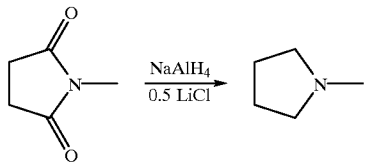

To a cooled solution of NaAlH$_4$ (0.22 mol) in toluene/THF under argon is added LiCl (0.11 mol) in THF. Note: LiCl can be added to the reactor prior to the addition of NaAlH$_4$ or after the addition of the substrate. N-methylsuccinimide (0.083 mol) in THF is added holding the temperature below 15° C. After addition is completed, reaction is allowed to warm to room temperature. After 30 minutes at room temperature reaction is heated to >40° C. for 2 hr. The reaction is then cooled to <5° C. and toluene (50 ml) is added. Water (9 ml) is then added slowly holding the temperature below 15° C. Additional H$_2$O or aqueous NaOH is used as necessary. The insoluble inorganic salts are removed by filtration. These solids are washed with additional THF or toluene to obtain a solution which contained N-methyl pyrrole, as determined by GLC analysis. Similar results were obtained using 0.02 mole of lithium chloride, but a longer heating period is required.

EXAMPLE 16

Reduction of N-methyl succinimide with NaAlH$_4$/Lithium t-butoxide.

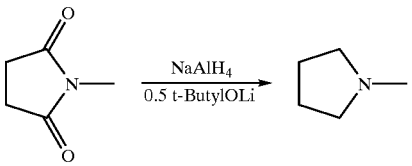

To a cooled solution of NaAlH$_4$ (0.22 mol) in toluene/THF under argon is added lithium tert-butoxide (0.11 mol) in THF. N-methylsuccinimide (0.083 mol) is added in THF (65 ml) holding the temperature below 15° C. After addition is complete, the reaction is allowed to warm to room temperature. After 30 minutes at room temperature, the reaction is heated to >40° C. for 2 hr. The reaction is then cooled to <5° C. and toluene (5 ml) is added. Water (9 ml) is then added slowly holding the temperature below 15° C. Additional H$_2$O or aqueous NaOH is used as necessary. The solid inorganic salts are removed by filtration. These solids are washed with additional THF or toluene to obtain solution which contained N-methyl pyrrole, as determined by GLC analysis.

It is understood that upon reading the above description of the present invention, one skilled in the art could make changes and variations therefrom. These changes and variations are included in the spirit and scope of the following appended claims.

That which is claimed is:

1. A process for the preparation of an unfiltered composition for the reduction of organic substrates, comprising the steps of, in sequence:

adding at least one Lewis base to at least one additive to form a preformed Lewis base/additive slurry; and thereafter adding a preformed slurry of at least one active hydride to said preformed Lewis base/additive slurry under conditions sufficient to form an unfiltered reduction composition having reducing properties.

2. The process of claim 1, wherein said preformed slurry of at least one active hydride comprises a slurry of said at least one active hydride in a hydrocarbon solvent.

3. The process of claim 1, wherein said reduction composition comprises a slurry.

4. The process of claim 3, further comprising heating the reduction composition slurry after the step of adding said preformed slurry of at least one active hydride to said Lewis base/additive slurry.

5. The process of claim 1, wherein said at least one additive is selected from the group consisting of lithium chloride, lithium bromide, aluminum trichloride, titanium tetrachloride, titanium tetrabromide, lithium alkoxides, lithium alkoxides of chiral alcohols, lithium dialkylamides, lithium dialkyl amides of chiral amines, and mixtures thereof.

6. The process of claim 5, wherein said at least one additive comprises lithium chloride.

7. The process of claim 1, wherein said at least one active hydride is selected from the group consisting of sodium aluminum hydride, trisodium aluminum hexahydride, and mixtures thereof.

8. The process of claim 7, wherein said at least one active hydride comprises sodium aluminum hydride.

9. The process of claim 1, wherein said at least one Lewis base is selected from the group consisting of tetrahydrofuran, 2-methyltetrahydrofuran, diethyl ether, dibutyl ether, methyl t-butyl ether (MTBE), 1,2-diethoxyethane, 1,2-dimethoxyethane, triethylamine, tributylamine, N, N, N', N'-tetramethylethylenediamine (TMEDA), diisopropylethylamine, and mixtures thereof.

10. The process of claim 9, wherein said at least one Lewis base comprises tetrahydrofuran.

11. The process of claim 1, wherein:

the step of adding at least one Lewis base to at least one additive comprises adding 45 to 80 mole % Lewis base to 5 to 20 mole % additive; and the step of adding said preformed slurry of at least one active hydride comprises adding 5 to 20 mole % active hydride.

12. A process for the preparation of an unfiltered composition for the reduction of organic substrates, comprising in sequence the steps of:

adding 45 to 80 mole % tetrahydrofuran to 5 to 20 mole % lithium chloride to form a preformed slurry thereof; and thereafter adding 5 to 20 mole % of a slurry of sodium aluminum hydride in a hydrocarbon solvent to said preformed tetrahydrofuran/lithium chloride slurry.

13. An unfiltered composition for the reduction of organic substrates, comprising an unfiltered composition by the process comprising the steps of, in sequence:

adding at least one Lewis base to at least one additive to form a preformed slurry thereof; and adding a slurry of at least one active hydride to said preformed Lewis base/additive slurry under conditions sufficient to produce a reduction composition having reducing properties.

14. The composition of claim 13, wherein the step of adding said slurry of at least one active hydride to said Lewis base/additive slurry comprises adding a slurry of said at least one active hydride in a hydrocarbon solvent to said Lewis base/additive slurry.

15. The composition of claim 13, wherein said at least one Lewis base comprises tetrahydrofuran, said at least one additive comprises lithium chloride and said at least one active hydride comprises sodium aluminum hydride, and wherein said reduction composition comprises a slurry.

16. An unfiltered composition for the reduction of organic substrates, comprising an unfiltered composition prepared by the process comprising the steps of, in sequence:

adding 45 to 80 mole % tetrahydrofuran to 5 to 20 mole % lithium cholride to form a preformed Lewis base/lithium chloride slurry; and adding 5 to 20 mole % of a preformed slurry of sodium aluminum hydride in a hydrocarbon solvent to said preformed tetrahydrofuran/lithium chloride slurry.

17. The composition of claim 13, wherein said composition exhibits substantially stable rate acceleration/runaway behavior until heated above 300° C.

18. The composition of claim 17, further comprising about 10 to about 11.5% Na, about 10 to about 11.5% Al, about 9 to about 10% Li and about 9 to about 10% Cl.

19. A process for reducing at least one functional group of an organic substrate, comprising:

adding at least one Lewis base to at least one additive to form a preformed Lewis base/additive slurry;

thereafter adding a preformed slurry of at least one active hydride to said preformed Lewis base/additive slurry under conditions sufficient to form an unfiltered reduction composition having reducing properties; and contacting said organic substrate with said unfiltered reduction composition.

20. The process of claim 19, wherein the organic substrate is (+/-) trans 3-ethoxycarbonyl-4-(4'-fluorophenyl)-N-methyl-piperidine-2,6-dione.

21. The process of claim 19, wherein the organic substrate is (+/-) trans 3-methoxycarbonyl-4-(4'-fluorophenyl)-N-methyl-piperidine-2,6-dione.

22. The process of claim 19, wherein the organic substrate is (-) trans 3-ethoxycarbonyl-4- (fluorophenyl)-N-methyl-piperidine-2,6-dione.

23. The process of claim 19, wherein the organic substrate is (-) trans 3-methoxycarbonyl-4- (4'fluorophenyl)-N-methyl-piperidine-2,6-dione.

24. The process of claim 19, wherein said preformed slurry of at least one active hydride comprises a slurry of sodium aluminum hydride in toluene, and said preformed Lewis base/additive slurry comprises more than 0.01 equivalents of lithium halide in tetrahydrofuran.

25. The composition of claim 13, wherein said composition comprises starting materials, counterion exchange products of said starting material, complexes of said starting materials, complexes of said counterion exchange products, and mixtures thereof.

26. The composition of claim 25, wherein said composition comprises a plurality of particles having a mean diameter of about 350 μm and a median diameter of about 400 μm.

27. The composition of claim 13, wherein said active hydride is sodium aluminum hydride and said additive comprises a lithium compound selected from the group consisting of lithium halides, lithium alkoxides and lithium organoamides, wherein said sodium aluminum hydride and said lithium compound ar present in a molar ratio ranging from about 2:1 up to about 10:1.

28. The process of claim 1, wherein said process is conducted without a catalyst.

* * * * *